(12) United States Patent
Chalekian

(10) Patent No.: US 9,119,715 B2
(45) Date of Patent: Sep. 1, 2015

(54) COLLAPSIBLE/EXPANDABLE PROSTHETIC HEART VALVE DELIVERY SYSTEM AND METHODS

(75) Inventor: Aaron J. Chalekian, Minneapolis, MN (US)

(73) Assignee: St. Jude Medical, Inc., St. Paul, MN (US)

( * ) Notice: Subject to any disclaimer, the term of this patent is extended or adjusted under 35 U.S.C. 154(b) by 625 days.

(21) Appl. No.: 13/126,847

(22) PCT Filed: Oct. 29, 2009

(86) PCT No.: PCT/US2009/005872
§ 371 (c)(1),
(2), (4) Date: Jun. 29, 2011

(87) PCT Pub. No.: WO2010/051025
PCT Pub. Date: May 6, 2010

(65) Prior Publication Data
US 2011/0257734 A1    Oct. 20, 2011

Related U.S. Application Data

(60) Provisional application No. 61/197,909, filed on Oct. 30, 2008.

(51) Int. Cl.
*A61F 2/24* (2006.01)
*A61F 2/95* (2013.01)
*A61F 2/958* (2013.01)

(52) U.S. Cl.
CPC .............. *A61F 2/2433* (2013.01); *A61F 2/958* (2013.01); *A61F 2/243* (2013.01); *A61F 2/2412* (2013.01); *A61F 2/2427* (2013.01); *A61F 2/95* (2013.01); *A61F 2002/9505* (2013.01); *A61F 2002/9522* (2013.01); *A61F 2002/9583* (2013.01)

(58) Field of Classification Search
USPC ................................................ 623/1.11, 2.11
See application file for complete search history.

(56) References Cited

U.S. PATENT DOCUMENTS 5,876,436 A    3/1999    Vanney et al.
6,719,790 B2    4/2004    Brendzel et al.
(Continued)

OTHER PUBLICATIONS

International Search Report and Written Opinion, PCT/US2009/005872 dated Dec. 17, 2009.

*Primary Examiner* — Dianne Dornbusch
*Assistant Examiner* — Robert Lynch
(74) *Attorney, Agent, or Firm* — Lerner, David, Littenberg, Krumholz & Mentlik, LLP

(57) ABSTRACT

A system for delivering a medical implant includes an expandable member at least partially positioned inside the medical implant and operable to radially expand at least a portion of the medical implant to an expanded condition, first and second grasping mechanisms each adapted to grasp a portion of the medical implant, and a displacement mechanism operatively coupled to the first and second grasping mechanisms and configured to move the first and second grasping mechanisms between an inner position in which the first and second grasping mechanisms are relatively close to one another, and an outer position in which the first and second grasping mechanisms are relatively distant to one another. The movement of the first and second grasping mechanisms from the outer position to the inner position at least partially collapses the medical implant from the expanded condition to enable the medical implant to be repositioned if necessary.

16 Claims, 7 Drawing Sheets

(56) References Cited

U.S. PATENT DOCUMENTS

| | | | |
|---|---|---|---|
| 2002/0042651 A1* | 4/2002 | Liddicoat et al. | 623/2.11 |
| 2002/0120277 A1 | 8/2002 | Hauschild et al. | |
| 2004/0087965 A1 | 5/2004 | Levine et al. | |
| 2005/0137689 A1* | 6/2005 | Salahieh et al. | 623/2.11 |
| 2005/0203614 A1* | 9/2005 | Forster et al. | 623/2.11 |
| 2006/0184226 A1 | 8/2006 | Austin | |
| 2007/0088431 A1* | 4/2007 | Bourang et al. | 623/2.11 |
| 2007/0203575 A1* | 8/2007 | Forster et al. | 623/2.11 |
| 2008/0249566 A1* | 10/2008 | Harris et al. | 606/220 |

* cited by examiner

COLLAPSIBLE/EXPANDABLE PROSTHETIC HEART VALVE DELIVERY SYSTEM AND METHODS

CROSS-REFERENCE TO RELATED APPLICATIONS

This application is a national phase entry under 35 U.S.C. §371 of International Application No. PCT/US2009/005872, filed Oct. 29, 2009, published in English, which claims the benefit of the filing date of U.S. Provisional Patent Application No. 61/197,909 filed Oct. 30, 2008, the disclosures of which are hereby incorporated herein by reference.

FIELD OF TEE INVENTION

The present disclosure relates to medical implant delivery systems and methods and, more particularly, to delivery systems and methods for positioning an expandable prosthetic heart valve or stent into a patient's heart or blood vessel.

BACKGROUND OF THE INVENTION

Prosthetic heart valves are usually implanted in the human heart to replace natural valves. These valves essentially function as check valves, permitting the blood to flow through the valves in a downstream direction, but blocking blood flow in a reverse or upstream direction. Some prosthetic heart valves include an annular valve housing or body with a central orifice and occluders. The orifice provides a passageway for the blood, and the occluders open and close to regulate the passage of blood. For instance, U.S. Pat. Nos. 5,876,436 and 6,719,790 describe in detail specific prosthetic heart valves. Both of these references are hereby incorporated herein by reference in their entireties.

Certain prosthetic heart valves are collapsible to a relatively small circumferential size. This kind of prosthetic heart valve can be delivered into a patient less invasively than valves that are not collapsible. For example, a collapsible valve may be delivered into the patient via tube-like delivery apparatus such as a catheter, a trocar, a laparoscopic instrument, or the like. This can avoid the need for a more invasive procedure such as full open-chest, open-heart surgery. When the collapsed valve has reached the desired implant site in the patient (e.g., at or near the annulus of the patient's heart valve that is to be effectively replaced by the prosthetic valve), the prosthetic valve can be re-expanded to full operating size and released from the delivery apparatus. Typically, in its full operating size, the prosthetic valve engages adjacent native tissue of the patient to firmly anchor itself in the patient.

Because valves of the type described above are basically implanted by remote control (because the valve is inside the patient at the far end of delivery apparatus that is manipulated and controlled from its proximal end outside the patient), it can be difficult to get the valve to exactly the right location in the patient before releasing it from the delivery apparatus. Improvements are therefore sought with respect to how such valves are deployed, e.g., so that the valve can be repositioned and/or differently deployed if deployment does not appear to be leaving the valve exactly where and how it should be deployed.

SUMMARY OF THE INVENTION

The present disclosure relates to a system for delivering and positioning a medical implant. This system generally includes an expandable member, a first grasping mechanism, a second grasping mechanism, and a displacement mechanism. The expandable member is at least partially positioned inside the medical implant and operable to radially expand at least a portion of the medical implant to an expanded condition. Each of the first and second grasping mechanisms is adapted to securely grasp at least a portion of the medical implant. The displacement mechanism is operatively coupled to the first and second grasping mechanisms and configured to move the first and second grasping mechanisms between a first position in which the first and second grasping mechanisms are relatively close to one another, and a second position in which the first and second grasping mechanisms are relatively distant to one another. The movement of the first and second grasping mechanisms from the second position to the first position at least partially collapses the medical implant from the expanded condition.

In another embodiment, the delivery system includes first and second grasping mechanisms, a tubular member, an inflatable member, and a conduit. Each of the first and second grasping mechanisms is adapted to securely grasp at least a portion of the prosthetic heart valve and includes a jaw section. The tubular member is assembled over a portion of the first and second grasping mechanisms and is movable between a first position in which the first and second grasping mechanisms are relatively close to one another, and a second position in which the first and second grasping mechanisms are relatively distant to one another. The inflatable member is at least partially positioned inside the prosthetic heart valve and operable to radially expand the prosthetic heart valve to an expanded condition. The conduit is disposed in fluid communication with the inflatable member for supplying an inflation fluid to the inflatable member.

The present disclosure further relates to a method of delivering and positioning an expandable medical implant inside a patient' body. This method includes positioning a first expandable member inside a body at a predetermined position close to a native annulus of a heart valve, the first expandable member being at least partially surrounded by a prosthetic heart valve, radially expanding the first expandable member such that the prosthetic heart valve only engages two diametrically-opposed portions of the native annulus of the heart valve, radially collapsing a portion of the prosthetic heart valve, repositioning the prosthetic heart valve relative to the native annulus of the heart valve, radially expanding the collapsed portion of the prosthetic heart valve, removing the first expandable member from the body, positioning a second expandable member at least partially within the prosthetic heart valve located inside the body, and radially expanding the second expandable member such that the prosthetic heart valve engages an entire inner periphery of the native annulus of the heart valve.

BRIEF DESCRIPTION OF THE DRAWINGS

Various embodiments of the presently disclosed delivery system are disclosed herein with reference to the drawings, wherein.

DETAILED DESCRIPTION

Figure 1:
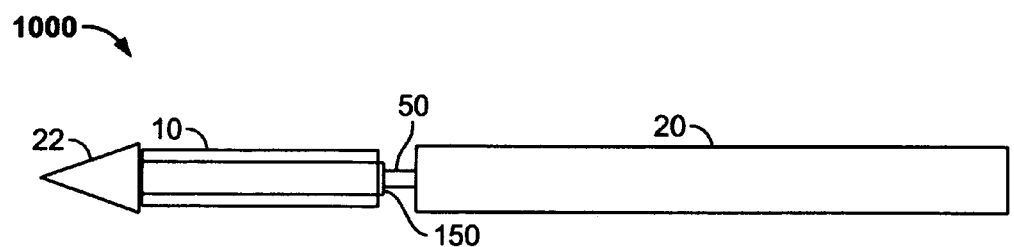
FIG. 1 is a highly schematic side view of a delivery system for positioning an expandable medical implant inside a patient's body.

Embodiments of the presently disclosed delivery systems are described herein in detail with reference to the drawing figures, wherein like reference numerals identify similar or identical elements. In the drawings and in the description which follows, the term "proximal", as is traditional, refers to the end of the delivery system, or portion thereof, which is closest to the operator, while the term "distal" refers to the end of the system, or portion thereof, which is farthest from the operator.

With reference to FIG. 1, the present disclosure relates to delivery systems and methods for deploying and positioning a collapsible and/or expandable medical implant, such as a prosthetic heart valve or stent, inside a patient's body. An embodiment of the delivery system is generally designated in FIG. 1 with reference number 1000. Although FIG. 1 shows delivery system 1000 operatively coupled to a prosthetic heart valve 10, delivery system 1000 can deploy any medical implant capable of expanding and/or collapsing. For instance, delivery system 1000 can deploy and position a stent within a patient's blood vessel. In some embodiments, the stent structure collapses to a smaller circumferential size by plastic deformation of components of the stent and plastically re-expands to a larger (full operating) circumferential size in response to expansion of an expandable member (for example, a balloon) temporarily placed inside the blood vessel.

Physicians can also employ delivery system 1000 for securely positioning prosthetic heart valve 10 in the native annulus of a heart valve. In certain embodiments, prosthetic heart valve 10 includes an annular (ring-like) stent structure (for example, of metal such as stainless steel) around or near its outer perimeter and one or more flexible valve leaflets (for example, of tissue or polymer sheet) attached within that structure. In use, delivery system 1000 allows prosthetic heart valve 10 to be repositioned in the patient if the accuracy of an initial deployment is less than ideal.

Delivery system 1000 may include a delivery sheath or tubular member 20, which may be a catheter, a trocar, a laparoscopic instrument, or any other structure suitable for percutaneously inserting an expandable medical implant inside a patient's body. Regardless of its specific structure, delivery sheath 20 has a longitudinal channel (not shown) extending along its long axis. This channel is sized for receiving prosthetic heart valve 10 in a collapsed state, a conduit 50, and an expandable member or mechanism 150 in a collapsed state. Conduit 50 can move longitudinally through sheath 20 and is operatively coupled to expandable member 150. As a result, expandable member 150 can move longitudinally between a retracted or proximal position and a deployed or distal position when conduit 50 moves along delivery sheath 20. In the retracted position, expandable member 150 is completely or partially enclosed within delivery sheath 20. In the deployed position, expandable member 150 is positioned outside delivery sheath 20, as seen in FIG. 1.

Some embodiments of delivery system 1000 incorporate a distal tip 22 positioned adjacent to the distal end of expandable member 150. In certain embodiments, distal tip 22 has an atraumatic configuration for facilitating insertion of delivery system 1000 into a patient's body. Although FIG. 1 depicts distal tip 22 with a substantially conical shape, distal tip 22 may have any other suitable shape, such as a bulbous shape. In several embodiments, distal tip 22 is attached to the distal end of conduit 50. See also FIG. 3.

Figure 2:
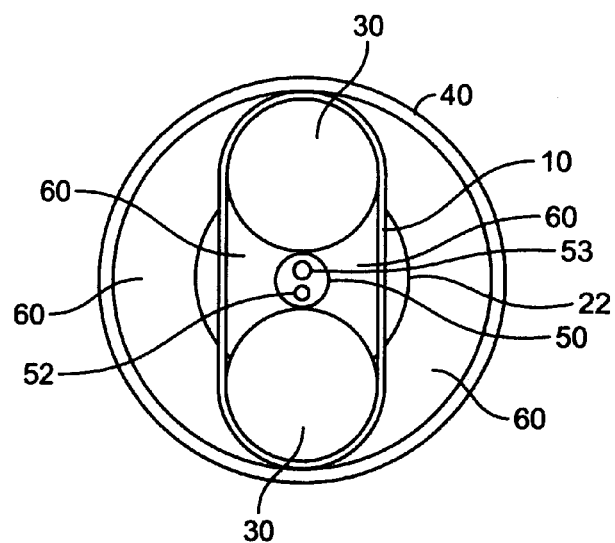
FIG. 2 is a cross-sectional view of the delivery system shown in FIG. 1, positioned inside a valve annulus of the patient.

As seen in FIG. 2, conduit 50 has two lumens 52, extending along its long axis. Lumen 52 may be dimensioned for receiving a guidewire (not shown), while lumen 53 may fluidly couple expandable member 150, such as one or more balloons 30, with a source of inflation fluid (not shown). Irrespective of whether expandable member 150 includes balloons 30, expandable member 150 can move from a collapsed state to an expanded state, thereby urging the expansion of prosthetic heart valve 10. Expandable member 150 may include two balloons 30 placed on diametrically-opposed sides of conduit 50, as shown in FIG. 2. Conduit 50 may include valves or other means allowing simultaneous or sequential inflation of balloons 30. In operation, balloons 30 inflate upon introduction of fluid through conduit 50, thereby expanding prosthetic heart valve 10. As shown in FIG. 2, each balloon 30 features a circular cross-section in its inflated state, but other embodiments may have other cross-sectional shapes.

When a nominal pressure is applied to balloons 30, prosthetic heart valve 10 expands and eventually engages diametrically-opposed portions of the native valve annulus (i.e., two areas of native valve annulus 40 that are 180° apart around the annulus), leaving voids 60 both inside and outside the confines of prosthetic heart valve 10. While the drawings show the middle portions of balloons 30 with substantially cylindrical shapes, balloons 30 may have any shape or configuration so long as they can cause prosthetic heart valve 10 to contact diametrically-opposed portions of valve annulus 40 upon inflation. Voids 60 allow the introduction of grasping mechanisms 100, as described in detail below.

Figure 3A:
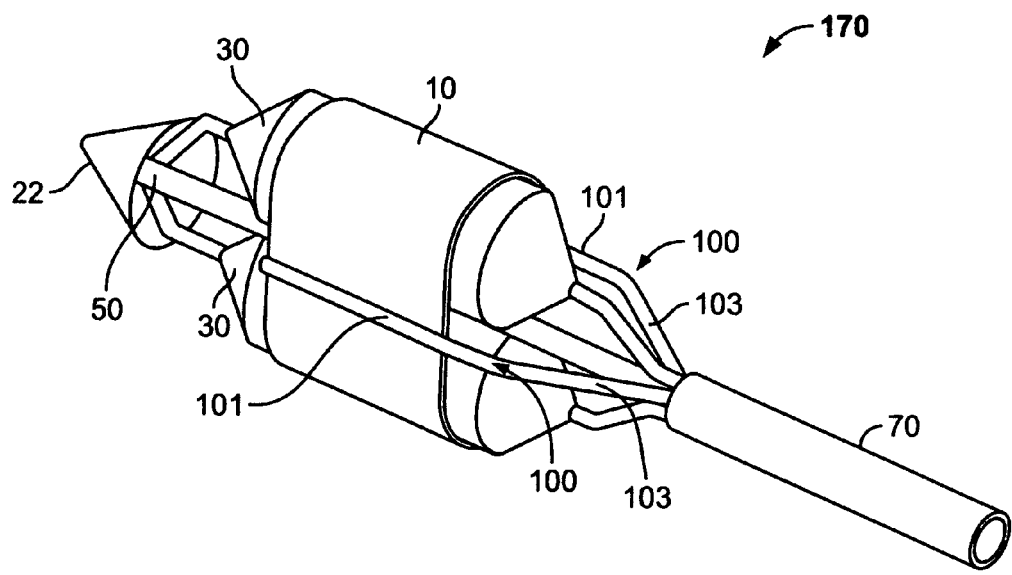
FIG. 3A is a perspective view of a portion of the delivery system depicted in FIG. 1, showing first and second grasping mechanisms in a first position.
Figure 3B:
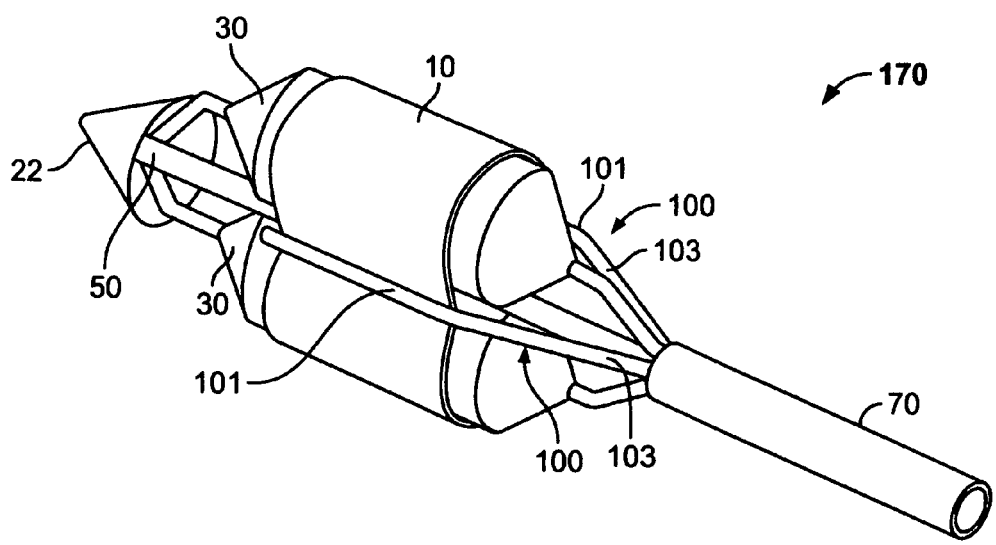
FIG. 3B is a perspective view of the portion of the delivery system illustrated in FIG. 3A, showing the first and second grasping mechanisms in a second position.

Referring to FIGS. 3A and 3B, delivery system 1000 further includes two or more grasping mechanisms 100 each adapted to grasp at least a portion of prosthetic heart valve 10. The first and second grasping mechanisms 100 are configured to move toward and away from each other between a first outward position (FIG. 3A) and a second inward position (FIG. 3B) upon actuation of a displacement mechanism 170 or any other suitable means. When the first and second grasping mechanisms 100 move from the outward position to the inward position, the portions of prosthetic heart valve 10 grasped by the grasping mechanisms move toward each other (i.e., toward central conduit 50), thereby squeezing prosthetic heart valve 10 radially inward. This action decreases the contact area between prosthetic heart valve 10 and native valve annulus 40, thereby decreasing the friction between the prosthetic valve and the valve annulus so that a user may easily reposition the prosthetic valve relative to the valve annulus. When grasping mechanisms 100 are moved to the inward position, the physician can reposition prosthetic heart valve 10. After repositioning prosthetic heart valve 10, the physician may return grasping mechanisms 100 to the outward position to anchor the prosthetic valve to native valve annulus 40. As grasping mechanisms 100 move to the outward position, the contact area between prosthetic heart valve 10 and native valve annulus 40 increases. Consequently, the friction between prosthetic heart valve 10 and native valve annulus 40 increases and, as a result, the prosthetic valve is fixed relative to the valve annulus.

As discussed above, displacement mechanism 170 can move the first and second grasping mechanisms 100 toward and away from each other. In some embodiments, displacement mechanism 170 includes a sheath or tubular member 70 surrounding at least proximal portions of the grasping mechanisms 100. These proximal portions of the grasping mechanisms 100 may have straight configurations which are oriented substantially parallel to each other. Distally of the proximal portions, each grasping mechanism 100 may include an outwardly angled arm 103. Displacement sheath 70 is configured to move longitudinally along at least portions of the first and second grasping mechanisms 100 between a proximal position (FIG. 3A) and a distal position (FIG. 3B). Moving displacement sheath 70 distally causes the grasping mechanisms 100 to move from the outward position to the inward position, thereby partially collapsing prosthetic heart valve 10, as discussed in detail below. Displacement sheath 70 may include a flare or tapered section at its distal end to facilitate its engagement with the angled arms 103 during distal translation.

As seen in FIGS. 3A and 3B, the first and second grasping mechanisms 100 are positioned between balloons 30 in voids 60 (FIG. 2), such that prosthetic valve 10 is sandwiched between the balloons and the grasping mechanisms. When balloons 30 are inflated, voids or spaces 60 are created both between the balloons and the expanded prosthetic valve 10, and between the expanded prosthetic valve and the valve annulus 40. The voids 60 formed between the prosthetic valve 10 and the balloons 30 allow the prosthetic valve to collapse when grasping mechanisms 100 move to the inward position (FIG. 3B).

Figure 4A:
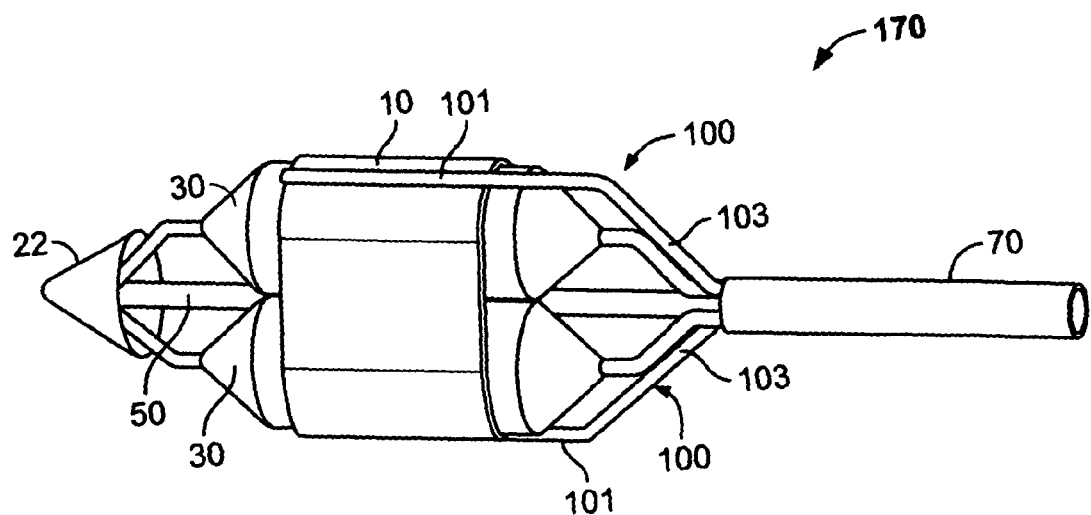
FIG. 4A is a perspective view of a second embodiment of the delivery system, showing the first and second grasping mechanisms in a first position.
Figure 4B:
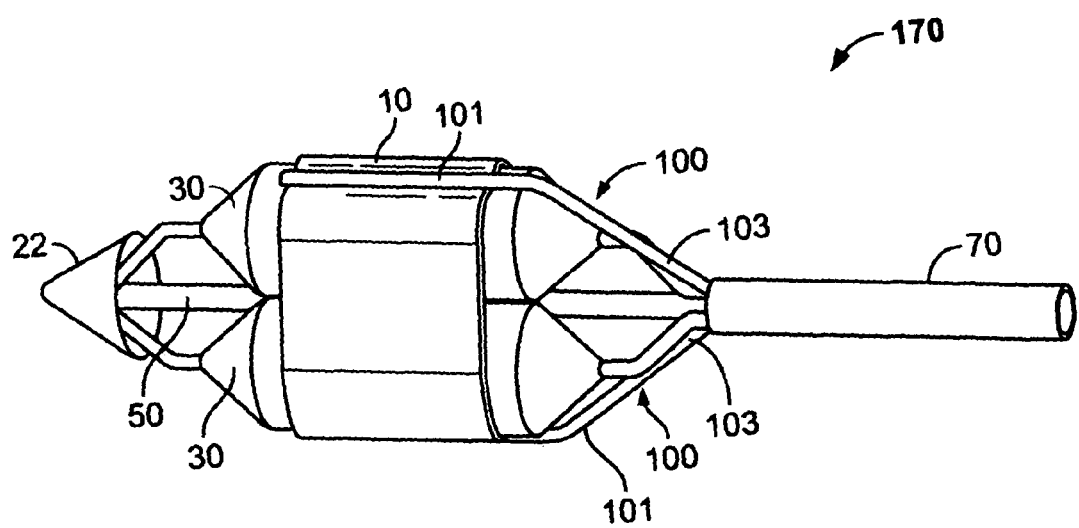
FIG. 4B is a perspective view of the delivery system depicted in FIG. 4A, showing the first and second grasping mechanisms in a second position.

In a variant of this embodiment, the first and second grasping mechanisms 100 may be positioned over an outer surface of balloons 30, as shown in FIGS. 4A and 4B. According to this variant, collapsing the grasping mechanisms 100 directly moves the expanded prosthetic valve 10 away from valve annulus 40, thereby enabling it to be repositioned by the physician. After repositioning prosthetic heart valve 10, grasping mechanisms 100 can be moved to the outward position, permitting the prosthetic valve to expand into firm engagement with the valve annulus, thereby fixing the position of the prosthetic valve relative to the valve annulus.

Figure 5A:
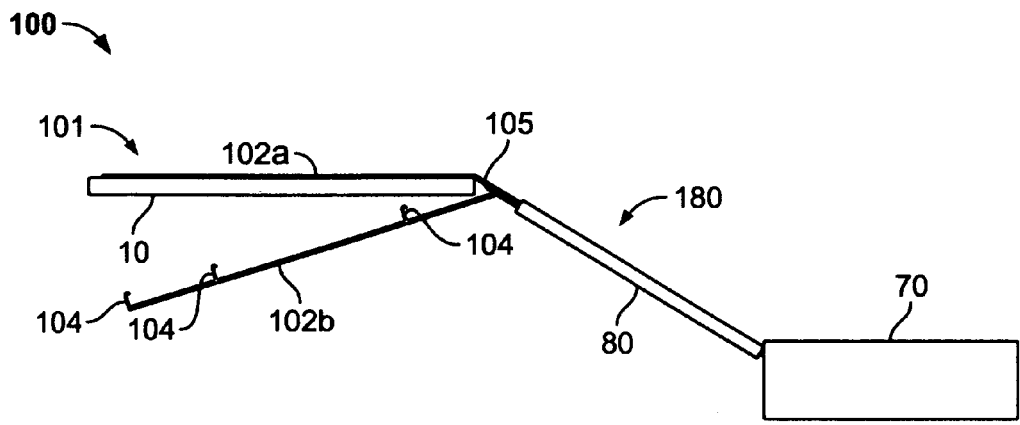
FIG. 5A is a highly schematic side view of a grasping mechanism with first and second jaw members in an open position.
Figure 5B:
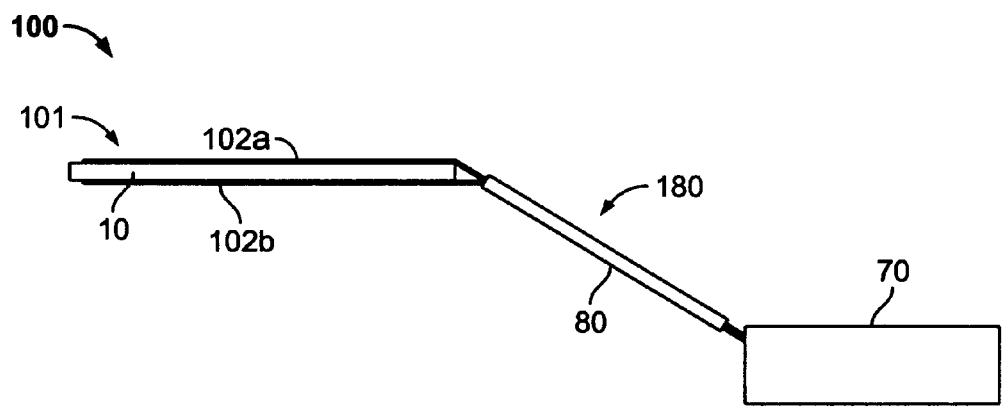
FIG. 5B is a highly schematic side view of the grasping mechanism of FIG. 5A with the first and second jaw members in a closed position.
Figure 5C:
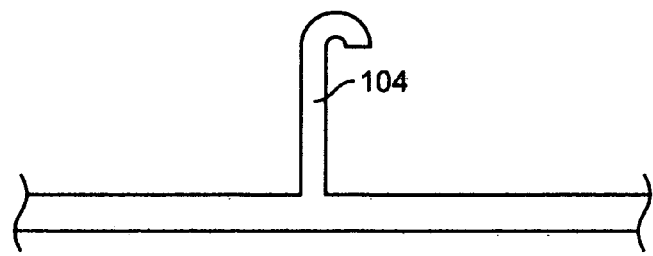
FIG. 5C is an enlarged side view of a portion of the second jaw member shown in FIG. 5A, illustrating a hook-shaped protrusion.

In preferred embodiments, at least one of the first and second grasping mechanisms 100 includes a jaw section 101 at its distal end. In highly preferred embodiments, each of grasping mechanisms 100 includes a jaw section 101 at its distal end. Jaw sections 101 are configured to grasp onto and clamp a wall of the prosthetic heart valve 10 to facilitate the positioning and repositioning of same relative to the native valve annulus 40. FIGS. 5A-5C show an embodiment of a jaw section 101 with a first or outer jaw member 102a and a second or inner jaw member 102b. The outer jaw member 102a has a smooth inner surface and, during use, engages an outer surface of prosthetic heart valve 10. The inner jaw member 102b is adapted to securely engage an inner surface of prosthetic heart valve 10 and, in some embodiments, may include one or more protrusions 104 spaced along its length. Protrusions 104 extend toward the outer jaw member 102a so as to engage the latticework of the prosthetic heart valve 10. One protrusion 104 may be located at a distal end of second jaw member 102b. In some embodiments, the free ends of the protrusions 104 may include a barb or a hook, as seen in FIG. 5C.

Outer and inner jaw members 102a, 102b may be pivotally connected to one another by a pivotal connection 105, such as a hinge, a pivot pin, or any other suitable structure or means. In an alternate arrangement, the inner jaw member 102b may be welded at an angle to the outer jaw member 102b so as to create a space therebetween. The inner jaw member 102b may pivot relative to the outer jaw member 102a at the point where the two meet, thereby defining pivotal connection 105. Pivotal connection 105 allows the outer and inner jaw members 102a, 102b to move toward and away from one another between an open or relaxed position (FIG. 5A) and a closed position (FIG. 5B). In the open position, the outer and inner jaw members 102a, 102b are spaced apart from one another so as to define an acute angle therebetween. The inner jaw member 102b may be resiliently biased to pivot away from the outer jaw member 102a to the open position. The inner jaw member 102b and/or pivotal connection 105 may be wholly or partly made of a shape-memory material, such as a nickel titanium alloy ("Nitinol"). This shape-memory material may be heat-set such that the inner jaw member 102b is resiliently biased away from the outer jaw member 102a at a normal human body temperature. In the closed position, the outer and inner jaw members 102a, 102b are oriented substantially parallel to one another.

With continued reference to FIGS. 5A-5C, each of first and second grasping mechanisms 100 includes a jaw closing mechanism 180 adapted to move the outer and inner jaw members 102a, 102b toward and away from one another. The jaw closing mechanism 180 may include an engagement sheath 80 surrounding at least a portion of the angled arm 103 of each grasping mechanism 100. Engagement sheath 80 may include a flare or a tapered section at its distal end for facilitating smooth engagement with the inner jaw member 102b and as the sheath moves along angled arm 103 from a proximal position (FIG. 5A) to a distal position (FIG. 5B), thereby moving the outer and inner jaw members 102a, 102b from the open position to the closed position, as discussed in detail below.

A user can utilize delivery system 1000 (and all other disclosed and envisioned embodiments) to accurately position an expandable medical implant, such as prosthetic heart valve 10, inside a patient's body. In an exemplary method, the user initially makes sure that balloons 30 are in a collapsed state, as shown in FIG. 1, and that grasping mechanisms 100 are in the outward position (see e.g., FIG. 3A or FIG. 4A). In this regard, delivery system 1000 preferably is preloaded with prosthetic heart valve 10 mounted in a collapsed condition around uninflated balloons 30, and grasping mechanisms 100 positioned on opposite sides of the prosthetic valve with the walls of the prosthetic valve positioned between jaw members 102a and 102b in the closed position. This entire assembly is then enclosed within delivery sheath 20. If the prosthetic heart valve 10 has not been preloaded in delivery system 1000, the user first secures the prosthetic valve around at least a portion of balloons 30 with grasping mechanisms 100.

In order to preload prosthetic heart valve 10 in delivery system 1000, the user places a portion of the prosthetic valve between the outer and inner jaw members 102a, 102b of one or more jaw sections 101. The engagement sheath 80 of each jaw section 101 is then moved distally along angled arm 103 from the proximal position (FIG. 5A) to the distal position (FIG. 5B). Upon distal translation, the engagement sheath 80 passes over the pivotal connection 105 and contacts at least a portion of the inner jaw member 102b, forcing it to pivot toward the outer jaw member 102a and into the closed position. As the inner jaw member 102b moves toward the outer jaw member 102a, protrusions 104 engage prosthetic heart valve 10, thereby minimizing any movement between the prosthetic valve and the jaw members. Subsequently, the user may move the entire assembly proximally or the delivery sheath 20 distally to enclose at least a portion of balloons 30 and the collapsed prosthetic heart valve 10 within the delivery sheath.

The user may then percutaneously insert a guidewire inside a patient's body until the distal end of the guidewire reaches a predetermined target (e.g., a location close to or at the annulus of the native valve). The location of the guidewire may be verified using any conventional imaging technique, such as fluoroscopy. The proximal portion of the guidewire should be exposed outside of the patient's body.

Once the distal end of the guidewire has reached the predetermined target, the user inserts the exposed proximal portion of the guidewire through lumen 52 of conduit 50 to position delivery system 1000 over the guidewire. The user may percutaneously advance delivery system 1000 distally over the guidewire to position the delivery sheath 20 at the predetermined target (for example, close to the native valve annulus).

When delivery sheath 20 has reached its desired destination, the physician may retract the delivery sheath 20 (or advance conduit 50 while holding the delivery sheath in place), thereby urging balloons 30 to their deployed position while maintaining them in an uninflated condition. Since prosthetic heart valve 10 is releasably secured around balloons 30, the prosthetic valve moves concomitantly with the balloons. The user may move conduit 50 longitudinally to position prosthetic heart valve 10 within native valve annulus 40 or at another desired site.

After prosthetic heart valve 10 has been positioned at what appears to be the proper location in the patient, the physician may inflate balloons 30, thereby radially expanding the prosthetic heart valve. When expandable member 150 includes balloons 30, balloons 30 are inflated to nominal pressure. To inflate balloons 30, inflation fluid is supplied to balloons 30 via lumen 52 of conduit 50. As seen in FIG. 2, the expansion of balloons 30 causes prosthetic heart valve 10 to expand and contact diametrically-opposed portions of native valve annulus 40 (i.e., in two areas that are 180° apart around the annulus). Thereafter, the user may slightly push delivery system 1000 in a distal direction to assess the engagement of prosthetic heart valve 10 with valve annulus 40.

The procedure for evaluating the placement of prosthetic heart valve 10 usually includes two queries. First, the user must evaluate whether the prosthetic heart valve 10 is located in an accurate position (sometimes referred as "evaluation inquiry A"). Second, the user must determine whether prosthetic heart valve 10 is in contact with annulus 40 (sometimes referred as "evaluation inquiry B").

If the answer to both evaluation inquiry A and evaluation inquiry B is yes, then subsequent steps may include deflating balloons 30 and removing them and grasping mechanisms 100 from prosthetic heart valve 10. Before removing the first and second grasping mechanisms 100, jaw sections 101 must be disengaged from prosthetic heart valve 10.

To release jaw sections 101 from prosthetic heart valve 10, the user moves engagement sheath 80 from the distal position (FIG. 5B) to the proximal position (FIG. 5A). The engagement sheath 80 consequently disengages from the inner jaw member 102b and, as a result, the inner jaw member 102b is biased to the relaxed or open position away from the outer jaw member 102a. Optionally, the user may push jaw section 101 distally while opening jaw members 102a, 102b to facilitate disengagement of the hook portions of protrusions 104 from the latticework of prosthetic heart valve 10. When the inner jaw member 102b moves away from the outer jaw member 102a, the prosthetic heart valve 10 is released from jaw section 101.

Once delivery system 1000 has been removed from prosthetic heart valve 10, a second expandable member, which may also be a balloon, may be inserted into the prosthetic valve. Unlike balloons 30, this second expandable member can contact the entire circumference of native valve annulus 40 when expanded. After positioning the second expandable member within prosthetic heart valve 10, the user expands the second expandable member to fully expand the prosthetic valve such that the entire periphery of the prosthetic valve engages the native valve annulus 40.

On the other hand, if the answer to evaluation inquiry A is no, then subsequent steps may include collapsing prosthetic heart valve 10, while keeping grasping mechanisms 100 in place, to enable the physician to reposition the prosthetic valve relative to native valve annulus 40. The physician may collapse diametrically opposed portions of prosthetic heart valve 10 by moving displacement sheath 70 along at least portions of the first and second grasping mechanisms 100 from the proximal position (FIG. 3A) to the distal position (FIG. 3B). When displacement sheath 70 is in the proximal position, it is spaced from arms 103 and jaw sections 101 are disposed in the outward position, exerting little if any inward force on prosthetic heart valve 10. To move jaw sections 101 to the inward position and therefore partially collapse prosthetic heart valve 10, the physician advances displacement sheath in a distal direction. During this distal advancement, displacement sheath 70 passes over at least a portion of the angled arms 103 of the first and second grasping mechanisms 100 and gradually forces these arms 103 toward one another. As angled arms 103 move toward one another, jaw sections 101 move toward one another as well. As a consequence, jaw sections 101 partially collapse prosthetic heart valve 10, as illustrated in FIG. 3B, decreasing the contact area between the prosthetic valve and native valve annulus 40. Since less of the prosthetic heart valve 10 engages the native valve annulus, the friction between the prosthetic valve and the valve annulus decreases. Such friction decrease allows the physician to reposition the prosthetic heart valve 10 to the desired location by rotating delivery system 1000 or moving it proximally or distally.

With prosthetic heart valve 10 properly positioned, displacement sheath 70 may be moved proximally to move jaw sections 101 away from one another, thereby anchoring the prosthetic valve to native valve annulus 40. The user may subsequently remove delivery system 1000 from prosthetic heart valve 10 as described above and insert a second expandable member (sized to achieve intimate contact between prosthetic heart valve 10 and the entire inner periphery of native valve annulus 40). This second expandable member may then be expanded to fully expand prosthetic heart valve 10 such that the entire periphery of the prosthetic valve engages the native valve annulus 40.

If the answer to evaluation inquiry B is no, the user may further expand or repeat the expansion of the second expandable member described above to achieve adequate apposition (i.e., contact between prosthetic heart valve 10 and native valve annulus 40).

After the above-mentioned second expandable member has been employed in any of the procedures discussed above, engagement sheaths 80 may be moved proximally to open jaw sections 101 and release prosthetic heart valve 10, as discussed in detail above. All of the components of delivery system 1000 may then be removed from the patient, leaving in place only the implanted and now-functioning prosthetic heart valve 10.

Figure 6:
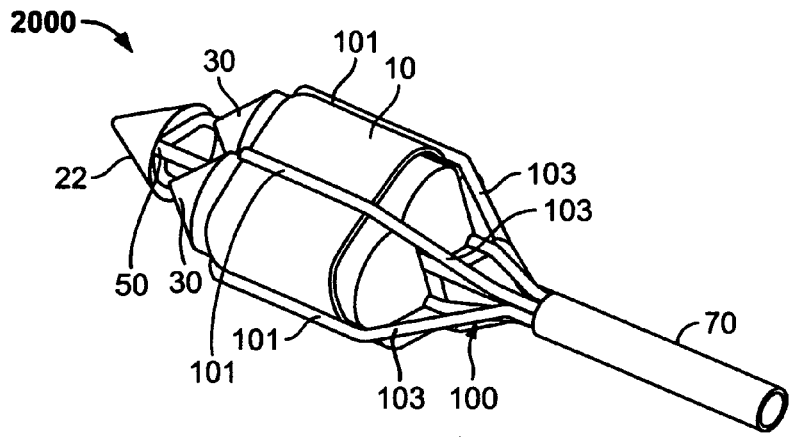
FIG. 6 is a perspective view of a third embodiment of the delivery system with four balloons and four grasping mechanisms, each grasping mechanism being located between two balloons.

Numerous modifications may be made to delivery system 1000 according to the present invention. In that regard, a delivery system 2000 in accordance with a second embodiment of the present invention is shown in FIG. 6. The structure and operation of delivery system 2000 are substantially similar to the structure and operation of delivery system 1000 described above. However, delivery system 2000 includes four balloons 30 arranged in a cross orientation and four grasping mechanisms 100. The four balloons 30 allow greater expansion of prosthetic heart valve 10 (as opposed to two balloons) and therefore provide a greater contact area between the prosthetic valve and native valve annulus 40. Since a greater portion of prosthetic heart valve 10 engages the native valve annulus when the four balloons are inflated, a more secure initial anchoring of the prosthetic valve to the valve annulus is achieved. The four balloons 30 also form voids therebetween when inflated. These voids allow the insertion of four grasping mechanisms 100 at four equally spaced locations around prosthetic heart valve 10. Hence, the four grasping mechanisms 100 grasp the prosthetic heart valve 10 at more locations than in delivery system 1000, thereby better securing the prosthetic valve to the delivery system 2000. Moreover, distributing the force required to move prosthetic heart valve 10 more uniformly around the circumference of the valve facilitates the movement of the valve and enables more accurate positioning of same in the valve annulus.

Figure 7:
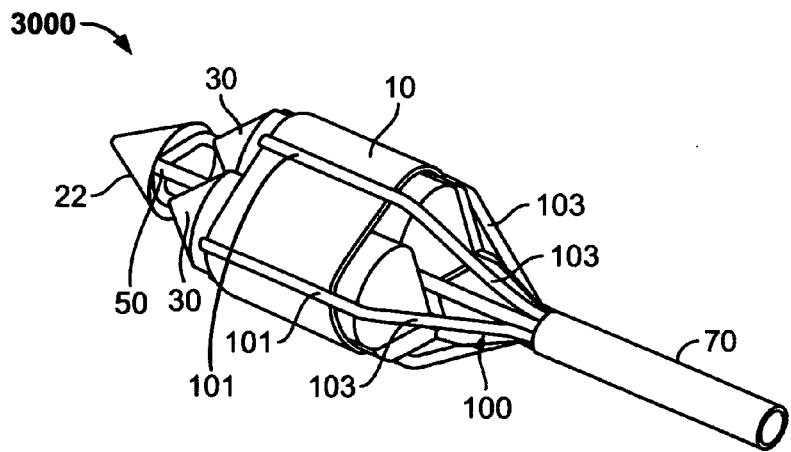
FIG. 7 is a perspective view of a fourth embodiment of the delivery system with four balloons and four grasping mechanisms, each grasping mechanism being located over a balloon.

FIG. 7 depicts a delivery system 3000 in accordance with a third embodiment of the present invention. The structure and operation of delivery system 3000 are substantially similar to the structure and operation of delivery system 2000 described above. However, rather than positioning grasping mechanisms 100 between balloons 30, the grasping mechanisms 100 in delivery system 3000 are each positioned over a balloon 30. This positioning enables the user to directly move portions of the prosthetic heart valve away from the native valve annulus, thereby further facilitating repositioning of the prosthetic valve.

Figure 8:
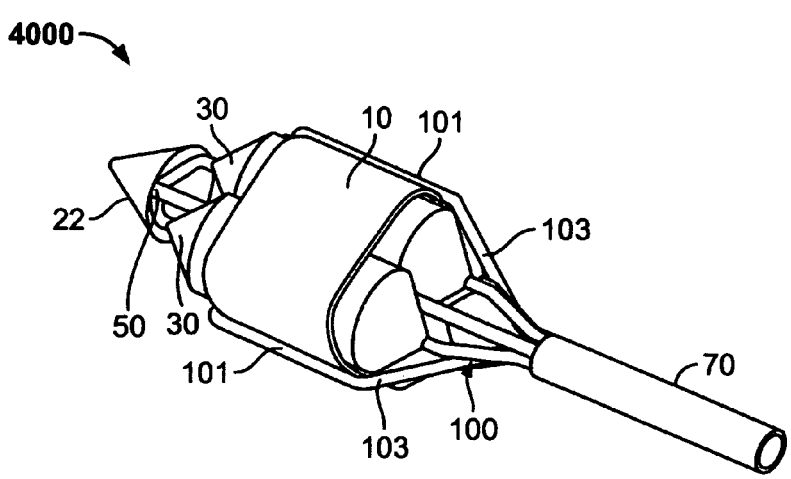
FIG. 8 is a perspective view of a fifth embodiment of the delivery system with four balloons and two grasping mechanisms, each grasping mechanism being located between two balloons.
Figure 9A:
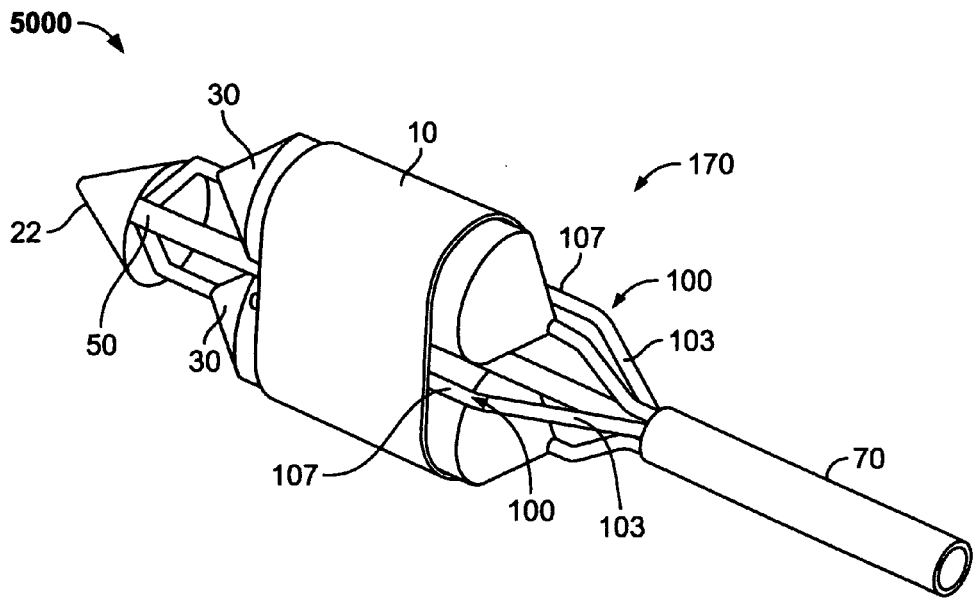
FIG. 9A is a perspective view of a sixth embodiment of the delivery system with two balloons and two grasping mechanisms, each grasping mechanism being located within the medical implant and in a first position.
Figure 9B:
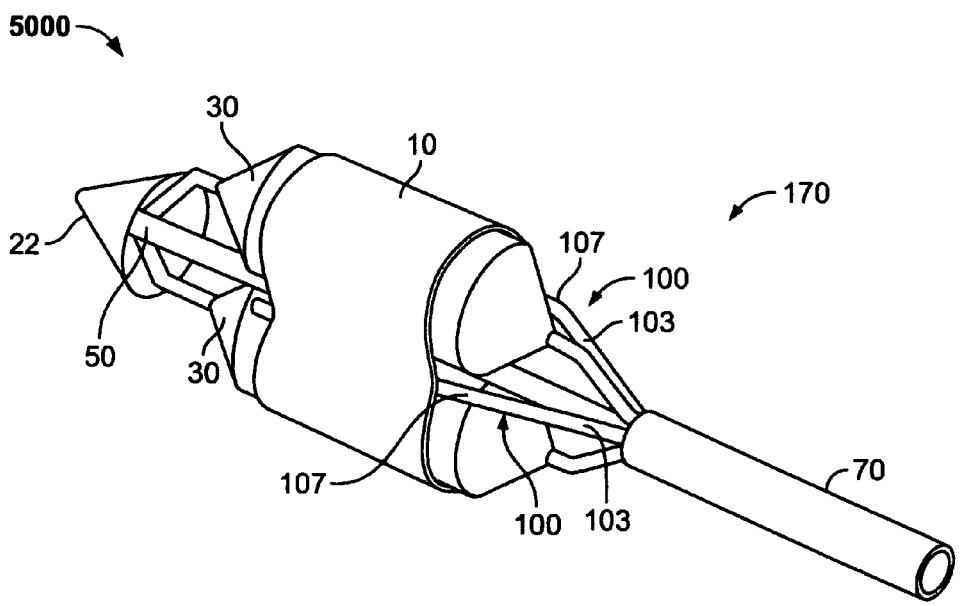
FIG. 9B is a perspective view of the delivery system depicted in FIG. 9A, showing the two grasping mechanisms in a second position.
Figure 9C:
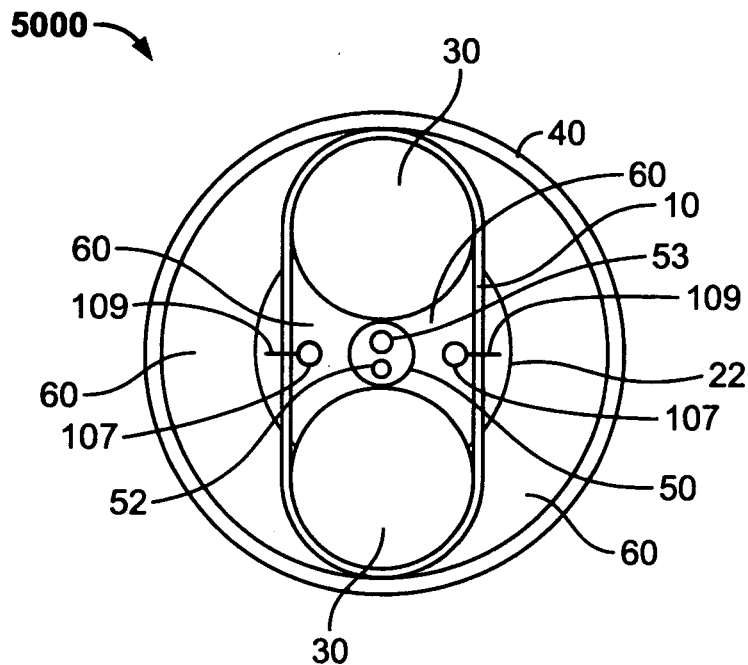
FIG. 9C is a cross-sectional view of the delivery system shown in FIG. 9A, positioned inside a valve annulus of the patient with the two grasping mechanisms in the first position.
Figure 9D:
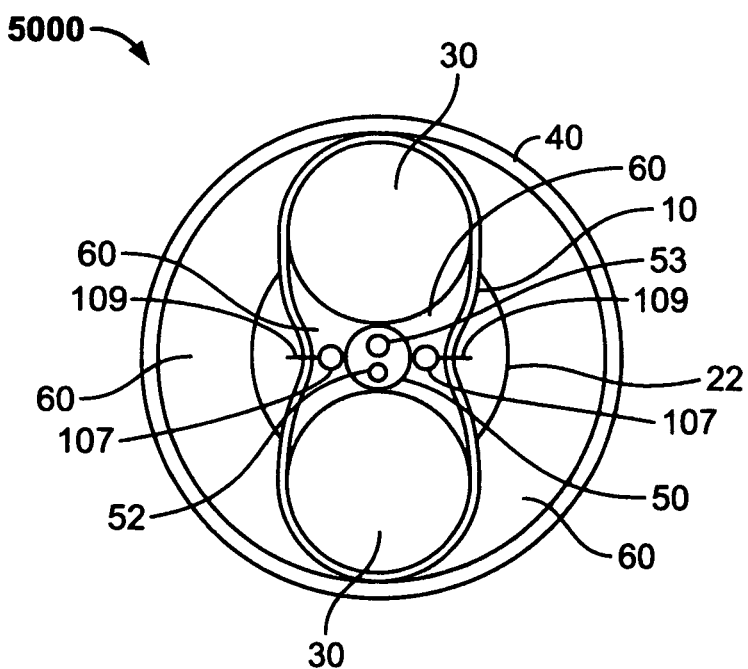
FIG. 9D is a cross-sectional view of the delivery system depicted in FIG. 9B, positioned inside a valve annulus of the patient with the two grasping mechanisms in the second position.

A delivery system 4000 in accordance with a fourth embodiment of the present invention is shown in FIG. 8. The structure and operation of delivery system 4000 are substantially similar to the structure and operation of the delivery system 2000 described above. However, rather than four grasping mechanisms 100, delivery system 4000 includes two grasping mechanisms 100 positioned in voids formed at opposite sides of the balloon assembly. As in delivery system 2000, the four balloons 30 allow greater expansion of prosthetic heart valve 10 (as opposed to two balloons) and therefore provide a greater contact area and a more secure initial anchoring between the prosthetic valve and native valve annulus 40. However, the provision of two grasping mechanisms 100 instead of four permits the cross-sectional size of delivery system 4000 to be minimized for percutaneous insertion through the patient's arterial system.

FIGS. 9A-9D illustrate a delivery system 5000 in accordance with a fifth embodiment of the present invention. The structure and operation of delivery system 5000 is substantially similar to the structure and operation of delivery system 1000 described above. However, delivery system 5000 includes two struts or elongate members 107 instead of jaw sections 101. Elongate members 107 are positioned within the voids 60 formed between prosthetic heart valve 10 and balloons 30, and each includes one or more protrusions 109 spaced along the length of each elongate member 107 and projecting outwardly toward the prosthetic valve. The free ends of protrusions 109 include a hook substantially similar to the hook on protrusions 104 shown in FIG. 5C. Protrusions 109 can secure to the latticework of the prosthetic heart valve 10 and pull the prosthetic valve inwardly when the grasping mechanisms 100 move from the outward position (FIGS. 9A and 9C) toward the inward position (FIGS. 9B and 9D), as discussed above. Delivery system 5000 has fewer moving parts than delivery system 1000 and therefore is easier and less costly to manufacture. Additionally, assembling elongate members 107 in the voids between the balloons 30 and prosthetic heart valve 10, with no structures outward of the prosthetic valve, enables the overall cross-section of delivery system 5000 to be minimized, thereby facilitating percutaneous insertion of same. It will be appreciated that elongate members 107 and outwardly projecting protrusions 109 may also be employed in delivery systems having four balloons, such as those described above in connection with delivery systems 2000, 3000 and 4000.

It will be appreciated that numerous other modifications may be made to the delivery system according to the present invention. For example, although the delivery systems have been described herein as having either two or four balloons 30 and either two or four grasping mechanisms 100, any number of balloons and grasping mechanisms may be used which will enable prosthetic heart valve 10 to be at least partially secured within native valve annulus 40 and temporarily released from such securement for repositioning. Additionally, while the invention has been described in connection with expandable members 150 in the form of balloons, any member may be used which is capable of being introduced percutaneously into the patient in a collapsed condition and subsequently expanded to at least partially expand prosthetic heart valve 10. Moreover, while the invention has been described in connection with the accurate positioning of a prosthetic heart valve 10 in native valve annulus 40, the apparatus and methods described herein may be used in a similar manner to accurately position any other collapsible stent structure in a body lumen.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A system for delivering and positioning a medical implant, comprising:
an expandable member at least partially positioned inside a medical implant and operable to radially expand at least a portion of the medical implant to an expanded condition;
a first grasping mechanism having a first movable arm adapted to grasp a first portion of the medical implant;
a second grasping mechanism having a second movable arm adapted to grasp a second portion of the medical implant, the first movable arm and the second movable arm being positioned on opposite sides of a longitudinal axis and on opposite sides of the expandable member so that the medical implant is sandwiched between the first and second movable arms and the expandable member;
the first and second movable arms each having a free end, at least one of the first and second movable arms including a jaw section on the free end thereof, the jaw section having an outer jaw member and an inner jaw member, the outer and inner jaw members being adapted to move between an open position in which the outer and inner jaw members are spaced apart from one another, and a closed position in which the outer and inner jaw members are relatively close to one another; and
a displacement mechanism operatively coupled to the first and second grasping mechanisms and configured to apply a force to the first grasping mechanism and the second grasping mechanism in directions orthogonal to the longitudinal axis to move the first movable arm and the second movable arm from an outer position in which the first and second movable arms are relatively distant to one another to an inner position in which the first and second movable arms are relatively close to one another;
wherein movement of the first and second movable arms from the outer position to the inner position at least partially collapses the medical implant from the expanded condition.

2. The system according to claim 1, wherein the displacement mechanism includes a displacement sheath surrounding at least a portion of the first and second grasping mechanisms, the displacement sheath being configured to move longitudinally along the first and second grasping mechanisms between a proximal position and a distal position.

3. The system according to claim 2, wherein movement of the displacement sheath from the proximal position to the distal position moves the first and second movable arms from the outer position to the inner position, and movement of the displacement sheath from the distal position to the proximal position moves the first and second movable arms from the inner position to the outer position.

4. The system according to claim 1, wherein the expandable member includes a balloon.

5. The system according to claim 1, wherein the expandable member includes a plurality of balloons.

6. The system according to claim 1, wherein the inner jaw member is resiliently biased away from the outer jaw member.

7. The system according to claim 1, wherein the inner jaw member is at least partly made of a shape memory material.

8. The system according to claim 1, further comprising an engagement sheath surrounding at least a portion of the at least one movable arm, the engagement sheath being translatable along the at least one movable arm between a proximal position and a distal position.

9. The system according to claim 8, wherein movement of the engagement sheath from the proximal position to the distal position moves the outer and inner jaw members from the open position to the closed position, and movement of the engagement sheath from the distal position to the proximal position moves the outer and inner jaw members from the closed position to the open position.

10. The system according to claim 1, wherein the inner jaw member includes at least one protrusion extending toward the outer jaw member.

11. The system according to claim 10, wherein a free end of the at least one protrusion includes a hook.

12. The system according to claim 1, further comprising third and fourth grasping mechanisms each adapted to grasp at least a portion of the medical implant.

13. The system according to claim 12, wherein the third grasping mechanism is positioned between the first and second grasping mechanisms and the fourth grasping mechanism is diametrically opposed to the third grasping mechanism.

14. The system according to claim 1, wherein the expandable member includes two balloons having inflated and deflated conditions, the balloons in the inflated condition defining spaces between the balloons and the medical implant, the first and second grasping mechanisms being positioned in the spaces.

15. A system for delivering and positioning a prosthetic heart valve inside a patient's body, comprising:
a first grasping mechanism having a first movable arm adapted to grasp a first portion of a prosthetic heart valve, the first movable arm having a free end and a first jaw section on the free end thereof, the first jaw section having an outer jaw member and an inner jaw member, the outer and inner jaw members being adapted to move between an open position in which the outer and inner jaw members are spaced apart from one another, and a closed position in which the outer and inner jaw members are relatively close to one another;
a second grasping mechanism having a second movable arm adapted to grasp a second portion of the prosthetic heart valve, the second movable arm having a free end and a second jaw section on the free end thereof, the second jaw section having an outer jaw element and an inner jaw element, the outer and inner jaw elements being adapted to move between an open position in which the outer and inner jaw elements are spaced apart from one another, and a closed position in which the outer and inner jaw elements are relatively close to one another, the first movable arm and the second movable arm being positioned on opposite sides of a longitudinal axis;

a tubular member assembled over a portion of the first and second grasping mechanisms and movable between a distal position in which the first and second movable arms are relatively close to one another, and a proximal position in which the first and second movable arms are relatively distant to one another, movement of the tubular member from the proximal position to the distal position applying a force to the first grasping mechanism and the second grasping mechanism in directions orthogonal to the longitudinal axis to move the first movable arm toward the second movable arm;

an inflatable member at least partially positioned inside the prosthetic heart valve and operable to radially expand the prosthetic heart valve to an expanded condition, the first movable arm and the second movable arm being positioned on opposite sides of the inflatable member so that the prosthetic heart valve is sandwiched between the first and second movable arms and the inflatable member; and a conduit disposed in fluid communication with the inflatable member for supplying an inflation fluid to the inflatable member.

16. The system according to claim 15, wherein the conduit is adapted to receive a guidewire.

* * * * *